US00PP17890P3

(12) United States Plant Patent

Slaughter et al.

(10) Patent No.: US PP17,890 P3

(45) Date of Patent: Jul. 31, 2007

(54) NECTARINE TREE 'BURNECTWENTYTHREE'

(50) Latin Name: *Prunus persica*
Varietal Denomination: Burnectwentythree

(75) Inventors: John K. Slaughter, Fresno, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 16 days.

(21) Appl. No.: 11/311,458

(22) Filed: Dec. 19, 2005

(65) Prior Publication Data

US 2007/0143886 P1 Jun. 21, 2007

(51) Int. Cl.
*A01H 5/00* (2006.01)

(52) U.S. Cl. ..... Plt./188

(58) Field of Classification Search ..... Plt./188
See application file for complete search history.

*Primary Examiner*—Kent Bell
*Assistant Examiner*—Annette H Para
(74) *Attorney, Agent, or Firm*—Wells St. John P.S.

(57) ABSTRACT

A new and distinct variety of nectarine tree (*Prunus persica* sub species *nuciperisica*), denominated varietally as 'Burnectwentythree', and which produces an attractively colored white-fleshed, non-melting, sub-acid, saucer-shaped, clingstone nectarine, which is mature for harvesting and shipment approximately June 12 to June 20 under ecological conditions prevailing in the San Joaquin Valley of central California.

1 Drawing Sheet

BACKGROUND OF THE NEW VARIETY

The present invention relates to a new, novel and distinct variety of nectarine tree, *Prunus persica* (subspecies *nuci-persica*), which has been denominated varietally as 'Burnectwentythree'.

The present variety of nectarine tree resulted from an on-going program of fruit and nut tree breeding. The purpose of this program is to improve the commercial quality of available deciduous fruit and nut varieties, and rootstocks, by creating and releasing promising selections of *prunus, malus* and *regia* species. To this end we make both controlled and hybrid cross pollinations each year in order to produce seedling populations from which improved progenies are evaluated and selected.

The seedling 'Burnectwentythree' was originated by us from a population of seedlings grown in our experimental orchards located near Fowler, Calif. The seedlings, grown on their own roots, were the result of a controlled cross made in February of 2000, of the yellow-fleshed peach tree 'Burpeachone' (U.S. Plant Pat. No. 12,156), which was used as the seed parent; and a sub-acidic, saucer-shaped nectarine tree 'Zhang Yu Pan' (unpatented) which was used as the pollen parent. One seedling which is the present variety, exhibited especially desirable characteristics, and was marked, 'J37.010' for subsequent observation. After the 2002 fruiting season, the new, present variety, was selected for advanced evaluation and repropagation.

ASEXUAL REPRODUCTION

Asexual reproduction of the new and distinct variety of nectarine tree was accomplished by budding the new nectarine tree to 'Nemaguard' Rootstock (un-patented). This was performed by us in our experimental orchard which is located near Fowler, Calif. Subsequent evaluations have shown those asexual reproductions run true to the original tree. All characteristics of the original tree, and its fruit, were established, and transmitted through succeeding asexual propagations.

SUMMARY OF THE VARIETY

'Burnectwentythree' is a new and distinct variety of nectarine tree, which is also a regular and productive bearer of relatively firm, sub-acidic white fleshed, non-melting, clingstone, saucer-shaped fruit which have a good flavor and eating quality. The tree of the present variety displays a medium low chilling requirement of approximately 550 hours. Still further, the present tree also produces relatively uniformly sized fruit throughout the tree. Additionally, the fruit produced by the present tree has a high degree of red skin coloration, a firm flesh and appears to have good handling and shipping qualities. The 'Burnectwentythree' Nectarine tree bears fruit which are ripe for commercial harvesting and shipment on approximately June 12 to June 20 under the ecological conditions prevailing in the San Joaquin Valley of central California. In relative comparison to the peach tree 'Burpeachone', which is the seed parent, the 'Burnectwentythree' Nectarine exhibits white flesh whereas the 'Burpeachone' exhibits yellow flesh. Additionally the present variety ripens approximately 2 weeks or more later than the peach tree 'Burpeachone'. In relative comparison to the nectarine tree 'Spring Bright' (U.S. Plant Pat. No. 7,507), which is the most similar variety known to the inventors at this time, the present new variety produces fruit which is white-fleshed and saucer-shaped whereas the 'Spring Bright' is yellow fleshed and globose shaped.

BRIEF DESCRIPTION OF THE DRAWINGS

The accompanying drawing, which is provided, is a color photograph of the new variety of nectarine tree. The photograph depicts three whole mature fruit, two of which are shown from a basal and apical perspective, and one whole fruit is seen from a lateral perspective displaying its saucer-like shape. Additionally one mature fruit is seen from the apical end, and is dissected substantially below the equatorial plane at the apical end, and which reveals the flesh characteristics. Also a typical stone, with the flesh removed to display the characteristic, has been provided. The external coloration of the fruit, as shown, is sufficiently matured for harvesting and shipment. The photograph also displays a sample vegetative shoot bearing typical leaves. The colors in the photograph are as nearly true as is reasonably possible in a color representation of this type. Due to chemical development, processing, and printing, the leaves and fruit depicted in these photographs may or may not be accurate when compared to the actual specimen. For this reason, future color references should be made to the color plates (Royal Horticultural Society) and the descriptions provided hereinafter.

DETAILED DESCRIPTION

Referring more specifically to the pomological details of this new and distinct variety of nectarine tree, the following has been observed during the fourth fruiting season under the ecological conditions prevailing at orchards located near the town of Fowler, county of Fresno, state of California. All major color code designations are by reference to The R.H.S. Colour Chart (Fourth Edition) provided by The Royal Horticultural Society of Great Britain. Common color names are also occasionally used.

NOT A COMMERCIAL WARRANTY

The following detailed description has been prepared to solely comply with the provisions of 35 U.S.C. § 112, and does not constitute a commercial warranty, (either expressed or implied), that the present variety will in the future display the botanical, pomological or other characteristics as set forth, hereinafter. Therefore, this disclosure may not be relied upon to support any future legal claims including, but not limited to, breach of warranty of merchantability, or fitness for any particular purpose which is directed, in whole, or in part, to the present variety.

Tree:

*Size.*—Generally — Considered medium-large as compared to other common commercial nectarine cultivars ripening in the early season of maturity. The tree of the present variety was pruned to a height of approximately 280.0 cm to about 300.0 cm at commercial maturity.

*Vigor.*—Considered moderately vigorous. The present variety grew from about 160.0 cm to 178.0 cm in height during the first growing season. The new nectarine tree variety was pruned to a height of approximately 150.0 cm during the first dormant season, and primary scaffolds were then selected for the desired tree structure.

*Productivity.*—Productive. Fruit set varies from 2.0 to several times more than the desired crop load. Fruit set is spaced by thinning to develop the remaining fruit into the desired market sized fruit. The number of the fruit set varies with prevailing climatic conditions, and the cultural practices employed during the bloom period, and are therefore not considered distinctive of this new variety.

*Bearer.*—Regular. Fruit set has been heavy, and thinning was necessary during the past 4 years.

*Form.*—Upright, and pruned into a vase shape.

*Density.*—Considered medium dense. It has been discovered that pruning the branches from the center of the tree to obtain a resulting vase shape allows for proper air movement in the tree, and appropriate amounts of sunlight to enhance fruit color and renewal of fruiting wood throughout the tree.

*Hardiness.*—The present tree was grown and evaluated in USDA Hardiness Zone 9. Winter chilling requirements of the new tree are approximately 550 hours below 7.0 degrees C. The variety hardy under typical central San Joaquin Valley climatic conditions.

Trunk:

*Diameter.*—Approximately 12.0 cm in diameter when measured at a distance of approximately 15.24 cm above the soil level, and at the end of the fourth growing season.

*Bark texture.*—Considered moderately rough, with numerous folds of papery scarfskin being present.

*Lenticels.*—Numerous flat, oval lenticels are present. The lenticels range in size from approximately 3.0 to about 6.0 millimeters in width, and from about 1.0 to about 2.0 millimeters in height.

*Lenticel color.*—Considered an Orange Brown, (RHS Greyed-Orange Group 164 B).

*Bark coloration.*—Variable, but it is generally considered to be grey-brown, (RHS Greyed-Orange Group 177 B).

Branches:

*Size.*—Considered medium for the variety.

*Diameter.*—Average as compared to other nectarine tree varieties. The branches have a diameter of about 6.0 centimeters when measured during the fourth year after grafting.

*Surface texture.*—Average, and appearing furrowed on wood which is several years old.

*Crotch angles.*—Primary branches are considered variable between about 47 to about 55 degrees from the horizontal axis. This particular characteristic is not considered distinctive of the variety, however.

*Current season shoots.*—Surface texture — Substantially glabrous.

*Internode length.*—Approximately 2.3 to about 2.5 cm. This tree characteristic is highly dependent upon plant nutrition, soil quality, pruning and other cultural practices, and therefore is not distinctive of the present variety.

*Color of mature branches.*—Medium brown, (RHS Greyed-Orange 174 A).

*Current seasons shoots.*—Color — Light green, (RHS Yellow-Green Group 144 C). The color of new shoot tips is considered a bright and shiny green (RHS Green Group 139 B).

Leaves:

*Size.*—Considered medium for the species. Leaf measurements have been taken from vigorous, upright, current-season growth, at approximately mid-shoot.

*Leaf length.*—Approximately 145.0 to about 152.0 millimeters.

*Leaf width.*—Approximately 31.0 to about 35.0 millimeters.

*Leaf base shape.*—Slightly oblique relative to the leaf longitudinal axis.

*Leaf form.*—Lancelolate.

*Leaf tip form.*—Acuminate.

*Leaf color.*—Upper Surface — Dark green, (approximately RHS Green Group 136 B).

*Leaf texture.*—Glabrous.

*Leaf color.*—Lower Surface — Medium green, (RHS Green Group 137 B).

*Leaf venation.*—Pinnately veined.

*Mid-vein.*—Color — Light yellow green, (RHS Yellow-Green Group 150 C).

*Leaf margins.*—Slightly undulating.

*Form.*—Considered crenate, occasionally doubly crenate.

*Uniformity.*—Considered generally uniform.

*Leaf petioles.*—Size — Considered medium long. Length — About 7.0 to about 10.0 cm. Diameter — About 2.0 to about 2.5 mm. Color — Pale green, (RHS Yellow-Green Group 150 C).

*Leaf glands.*—Size — Generally considered small. About 1.0 mm in height, and about 1.0 mm in width. Number — Generally one per side, occasionally two per side. Type — Considered reasonably unappressed relative to the petiole margin and moderately small. The leaf glands are globose in shape. The leaves are considered to be early deciduous. Color — Depending upon the developmental stage, the color is generally considered a brownish yellow. (RHS Greyed-Yellow Group 162 B).

*Leaf stipules.*—Size — Medium for the variety. Number — Typically 2 per leaf bud, and up to 6 per shoot tip. Form — Lanceolate in form, and having a serrated margin. Color — Green, (RHS Green Group 141 B) when young, but graduating to a brown color, (RHS Greyed-Orange group 165 A) with advancing senescence. The stipules are considered to be early deciduous.

Flower:

*Flower buds.*—Generally — The floral buds, depending upon the stage of development, are approximately 8.0 millimeters wide; and about 12.0 millimeters long; conic in form; and slightly appressed relative to the bearing shoot.

*Flower buds.*—Color — The bud scales, in an advanced, pre-bloom stage, are generally considered a reddish-brown, (approximately RHS Greyed Purple Group N186 C). The buds are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress, and therefore this information is not available.

*Date of first bloom.*—Observed on Feb. 24, 2005. The date of first bloom is somewhat dependent upon the prevailing climatic conditions.

*Blooming time.*—Considered mid-season in relative comparison to other commercial nectarine cultivars grown in the central San Joaquin Valley. Date of full bloom was observed on Mar. 2, 2005. The date of bloom varies slightly with the prevailing climatic conditions, and cultural practices.

*Duration of bloom.*—Approximately 8 days. This characteristic varies slightly with the prevailing climatic conditions.

*Flower type.*—The variety is considered to have a non-showy type flower.

*Flower size.*—Flower diameter at full bloom is approximately 30.0 to about 34.0 millimeters.

*Bloom quantity.*—Considered very abundant.

*Flower bud frequency.*—Normally 1 to 2 flower buds appear per node.

*Petal size.*—Generally — Considered small for the species but considered medium for the flower type.

*Length.*—Approximately 14.0 to about 16.0 millimeters.

*Width.*—Approximately 7.0 to about 10.0 millimeters.

*Petal form.*—Elongated.

*Petal count.*—Generally 5.

*Petal texture.*—Glabrous.

*Petal color.*—Light pink, (RHS Red-Purple Group 65 B), to a medium pink, (RHS Red-Purple Group 65 A).

*Fragrance.*—Slight.

*Petal claw.*—Form — The claw is considered elongated in shape, and has a relatively large size when compared to the overall dimensions of the petal itself. Length — Approximately 10.0 to about 12.0 millimeters. Width — Approximately 4.0 to about 6.0 millimeters.

*Petal margins.*—Generally considered variable, from nearly smooth, to moderately undulate.

*Petal apex.*—Generally — The petal apices generally appear entire and without an apical groove.

*Flower pedicel.*—Length — Considered medium-long, and having an average length of approximately 5.0 to about 6.0 millimeters. Diameter — Considered average, approximately 2.0 millimeters. Color — A pale green, (RHS Greyed-Green Group 194 B).

*Floral nectaries.*—Color — Depending upon the stage of floral development, the color is considered to be a pale greenish brown, (RHS Greyed-Green Group 197 B), at a location which is near to the calyx base, and which further graduates to a greenish yellow color (Greyed-Yellow Group 160 A).

*Calyx.*—Surface Texture — Generally glabrous. Color — A dull red, (approximately RHS Greyed-Purple Group 187 B).

*Sepals.*—Surface Texture — The surface has a short, fine, pubescent texture. Size — Average, and ovate in form. Color — A dark reddish purple, (approximately RHS Greyed-Purple Group 187 C).

*Anthers.*—Generally — Large in size. Color — Red to reddish purple, (approximately RHS Greyed-Purple Group 187 D).

*Pollen production.*—Pollen is abundant, and has a yellow color, (approximately RHS Yellow Group 11 A).

*Filaments.*—Size — Variable in length, approximately 15.0 to about 19.0 millimeters in length. Color — Considered a pale pink, (RHS Red-Purple Group 65 C).

*Pistil.*—Number — Usually 1, occasionally 2. Generally — Average in size. Length — Approximately 17.0 to about 20.0 millimeters in length, including the ovary. Color — Considered a very pale green, (approximately RHS Yellow-Green Group 145 C). Surface Texture — The variety has a long glabrous pistil.

Fruit:

*Maturity when described.*—Firm ripe condition (shipping ripe). Date of first picking — Jun. 12, 2005. Date of last picking — Jun. 22, 2005. The date and duration of harvest varies slightly with prevailing climatic conditions.

*Size.*—Generally — Considered relatively large, and uniform.

*Average cheek diameter.*—Approximately 67.0 to about 74.0 millimeters.

*Average axial diameter.*—Approximately 22.0 to about 32.0 millimeters.

*Typical weight.*—Approximately 180.0 grams. This characteristic is highly dependent upon cultural practices, and therefore is not particularly distinctive of this new variety.

*Fruit form.*—Generally saucer-shaped. The fruit is generally uniform with occasional lobbing which appears to slightly favor one hemisphere when viewed from an apical perspective.

*Fruit suture.*—Very shallow, and extending from the base to the apex.

*Suture.*—Color — The background color appears to be white, (approximately RHS White Group 155 C), with some occasional red coloration, (approximately RHS Red Group 47 B).

*Ventral surface.*—Form — Short, abbreviated.

*Apex.*—Indented.

*Base.*—Broad.

*Stem cavity.*—Rounded, relatively large and relatively shallow. The average depth of the stem cavity is about 1.45 cm. The average width of the stem cavity is about 1. cm.

*Fruit skin.*—Thickness — Considered medium in thickness, and tenacious to the flesh. Texture — Glabrous. Occasional speckling observed on the skin particularly toward the apical end. Taste — Non-astringent. Tendency to crack — Rarely observed. Occasional russeting has been observed in some past years.

*Color.*—Blush Color — The blush color is variable from a medium red, (approximately RHS Red Group 44 C) to a dark red, (approximately RHS Red Group 46 A). The blush color ranges from about 70% to about 90% of the fruit surface depending upon the sunlight exposure and the prevailing growing conditions. Ground Color — Generally a light yellow, (approximately RHS Yellow White Group 158 D).

*Fruit stem.*—Moderate in length, approximately 6.0 to about 7.0 millimeters.

*Diameter.*—Approximately 3.0 to about 4.0 millimeters.

*Color.*—Light tan, (approximately RHS Greyed-Orange Group 164 D).

*Flesh.*—Ripens — Evenly. Texture — Firm, and dense. Considered non-melting. Fibers — Infrequently noted. Aroma — Moderately fragrant. Eating Quality — Considered very good. Flavor — Considered sweet and sub-acidic. The flavor is considered pleasant. Juice — Moderate. Brix — About 16.5 degrees. This characteristic varies slightly with the number of fruit per tree; the prevailing cultural practices; and the surrounding climatic and environmental conditions. Flesh Color — Pale white, (approximately RHS White Group 155 A).

Stone:

*Type.*—Clingstone.

*Size.*—Considered medium-small in relative comparison to other saucer-type varieties. The stone size varies with the resulting crop load, and tree vigor, and therefore is not considered a distinguishing characteristic of this new variety.

*Length.*—Average, about 11.5 to about 15.0 millimeters.

*Width.*—Average, about 17.0 to about 22.0 millimeters.

*Diameter.*—Average, about 19.0 to about 22.0 millimeters.

*Form.*—Oblate.

*Base.*—The stone's base is usually perpendicular to the stone's vertical axis.

*Apex.*—Shape — The stone apex has a slight tip.

*Stone surface.*—Surface Texture — The surface texture is generally characterized by a furrowed pattern which begins from the basal end. Substantial grooving over the apical shoulders is evident. Surface pitting is generally more frequent from the mid-section toward the apex of the stone. Ridges — The surface textures are generally rounded. Ventral Edge — Width — Considered medium large, and having a dimension of approximately 3.0 to about 4.0 millimeters when measured at mid-suture. The wings are most prominent over the suture line. Dorsal Edge — Shape — Full, heavily grooved, and having relatively smooth edges.

*Stone color.*—The color of the dry stone is a pale orange (Greyed-Orange Group approximately RHS N170 B).

*Tendency to split.*—Splits have occasionally been noted.

*Kernel.*—Generally — The kernel is considered poorly shaped, and often is observed with a shrivelled appearance especially toward the basal end of the kernel. It is common in saucer-shaped fruit to have a poorly formed endocarp due, at least in part, to the limited space which is available with the mesocarp. Form — Generally considered oblate. Pellicle — Pubescent. Color — Considered to be a pale brown (Greyed Brown Group 162 B).

*Use.*—The subject variety 'Burnectfourteen' is considered to be a Nectarine tree which matures early in the season, and which produces fruit, which are considered firm, attractively colored, and which are useful for both local and long distance shipping.

*Keeping quality.*—Excellent. Fruit has stored well at a temperature of about 1.0 degree Celsius for up to 25 days or more after harvest.

*Shipping quality.*—Good. The fruit of the new nectarine tree variety showed minimal bruising of the flesh, or skin damage, after being subjected to normal harvest and packing procedures.

*Resistance to insects and disease.*—No particular susceptibilities were noted. The present variety has not been tested to expose or detect any susceptibilities or resistances to any known plant and/or fruit diseases.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety nectarine tree, what we claim is new and desired to secure by Plant Letters Patent is:

1. A new distinct variety of nectarine tree, substantially as illustrated and described, and which is characterized principally as to novelty by producing an attractively colored, white-fleshed, non-melting, sub-acid, saucer-shaped clingstone nectarine which is mature for harvesting and shipment approximately June 12 to June 20 under the ecological conditions prevailing in the San Joaquin Valley of central California.

* * * * *

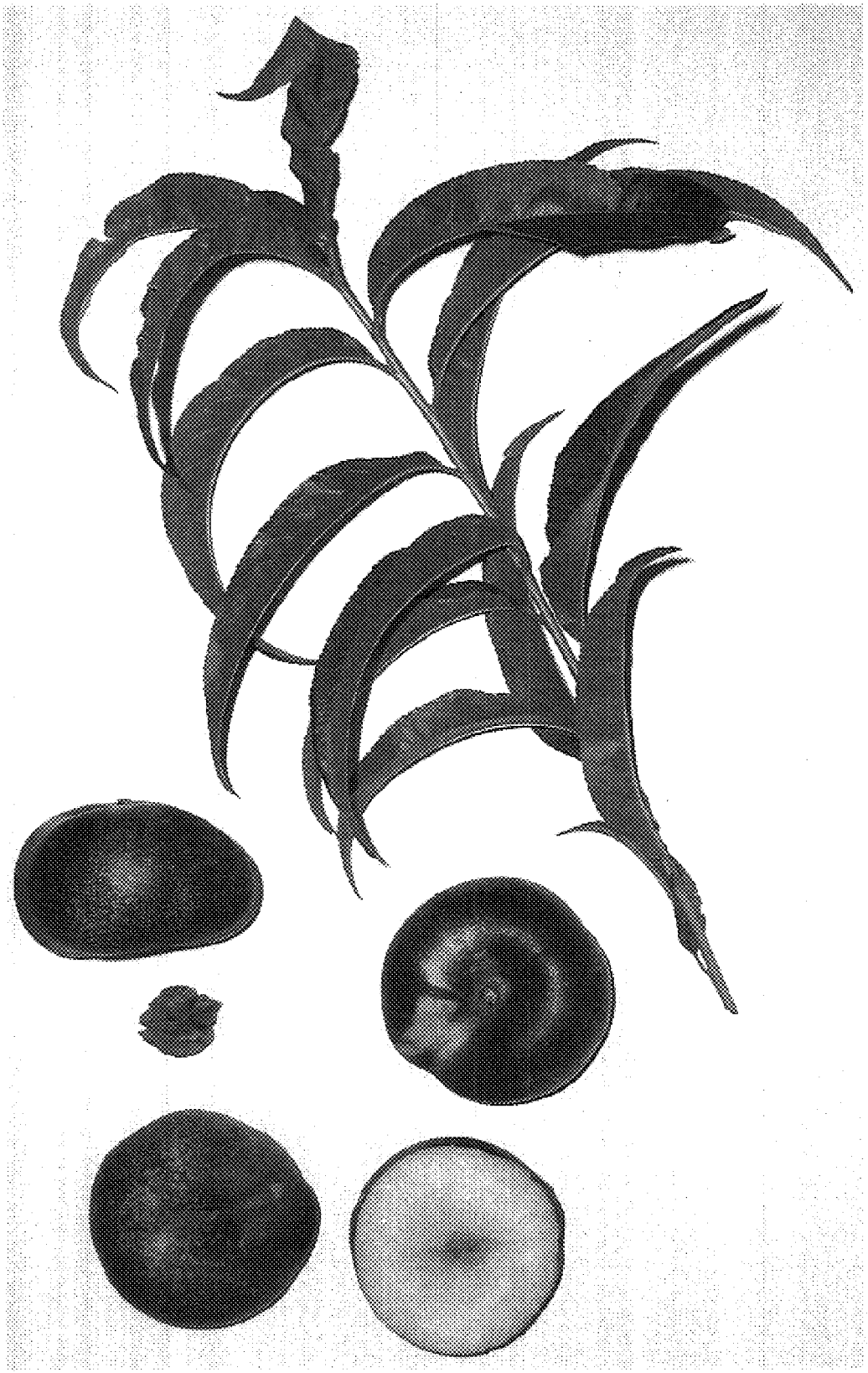

UNITED STATES PATENT AND TRADEMARK OFFICE

CERTIFICATE OF CORRECTION

PATENT NO. : PP 17,890 P3
APPLICATION NO. : 11/311458
DATED : July 31, 2007
INVENTOR(S) : John K. Slaughter et al.

It is certified that error appears in the above-identified patent and that said Letters Patent is hereby corrected as shown below:

Column 5, line 15, please replace “10.0 cm.” with --10.0 mm.--.

Signed and Sealed this

First Day of July, 2008

JON W. DUDAS
*Director of the United States Patent and Trademark Office*